United States Patent [19]

Klein et al.

[11] Patent Number: 4,692,329

[45] Date of Patent: * Sep. 8, 1987

[54] ERYTHROMYCIN/BENZOYL PEROXIDE ANTIACNE COMPOSITIONS

[75] Inventors: Robert W. Klein, Blue Bell, Pa.; Mary E. Foxx, Plainsboro, N.J.

[73] Assignee: William H. Rorer, Inc., Fort Washington, Pa.

[*] Notice: The portion of the term of this patent subsequent to Jun. 7, 2000 has been disclaimed.

[21] Appl. No.: 627,351

[22] Filed: Jul. 3, 1984

Related U.S. Application Data

[63] Continuation of Ser. No. 455,283, Jan. 3, 1983, Pat. No. 4,497,794, which is a continuation of Ser. No. 214,124, Dec. 8, 1980, abandoned, which is a continuation-in-part of Ser. No. 843,007, Oct. 17, 1977, abandoned, which is a continuation of Ser. No. 637,613, Dec. 4, 1975, abandoned.

[51] Int. Cl.⁴ .................... A61K 31/70; A61K 31/78
[52] U.S. Cl. ........................................ 424/81; 514/29; 514/714; 514/859
[58] Field of Search ................ 424/81, 338, 181; 514/29, 714

[56] References Cited

U.S. PATENT DOCUMENTS 4,056,611  11/1977  Young ................................ 424/62
4,387,107   6/1983  Klein et al. ...................... 424/338
4,497,794   2/1985  Klein et al. ....................... 424/81

OTHER PUBLICATIONS

Fulton, Arch, Dermatol/vol. 110, 7-1974, pp. 83-86.
Merck, Index, 9th Ed., 1976, p. 3288.

Primary Examiner—Leonard Schenkman
Attorney, Agent, or Firm—James A. Nicholson; Alexis Barron; Martin F. Savitzky

[57] ABSTRACT

Process and composition for the topical treatment of acne which comprises as ingredients a peroxide of an organic acid and an erythromycin compound selected from the group consisting of erythromycin and its stearate and glucoheptonate derivatives and in which said peroxide is from one-half to thirty times, the weight of said erythromycin compound, and a suitable pharmaceutically acceptable carrier.

7 Claims, 4 Drawing Figures

U.S. Patent  Sep. 8, 1987  4,692,329
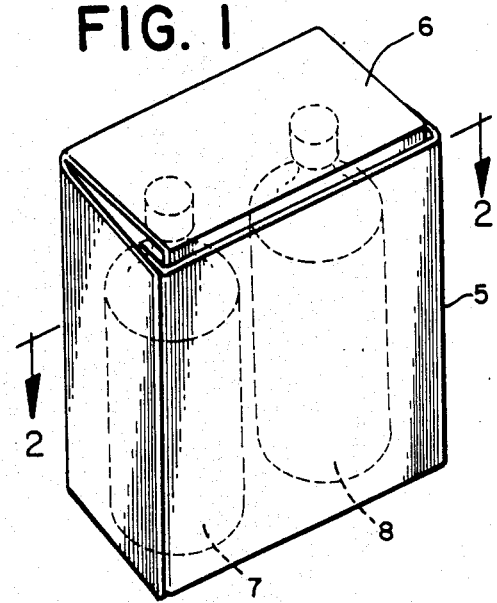
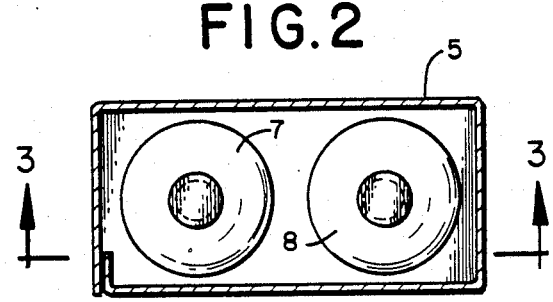
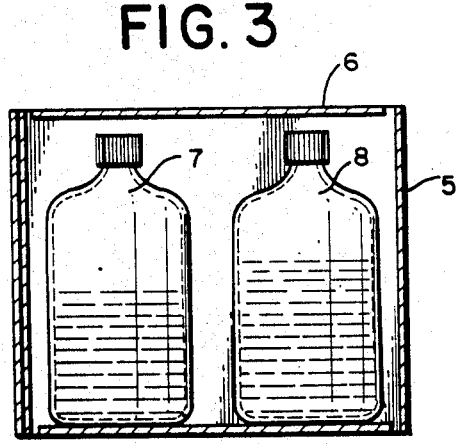
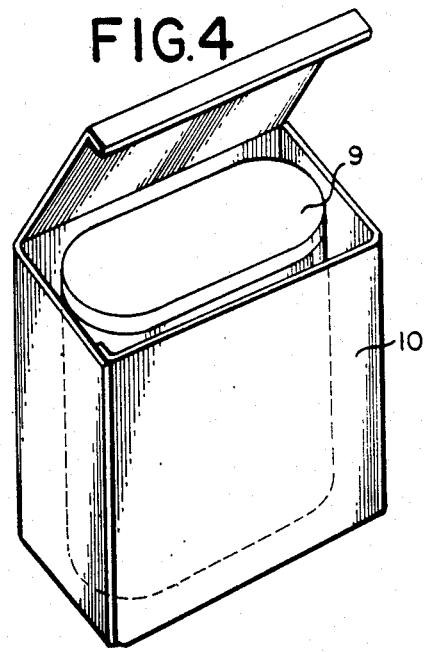

ERYTHROMYCIN/BENZOYL PEROXIDE ANTIACNE COMPOSITIONS

CROSS-REFERENCE TO RELATED APPLICATIONS

This is a continuation of Ser. No. 455,283, filed Jan. 3, 1983, now U.S. Pat. No. 4,497,794, which is a continuation of Ser. No. 214,124, filed Dec. 8, 1980, now abandoned, which is a continuation-in-part of Ser. No. 843,007, filed Oct. 17, 1977, now abandoned, which is a continuation of Ser. No,. 637,613, filed Dec. 4, 1975 now abandoned.

FIELD OF THE INVENTION

This invention relates to pharmaceutical preparations and particularly to active ingredients which are useful for the topical treatment of acne. The invention also includes a method of treatment of humans with the pharmaceutical preparations and ingredients to medicinally treat acne.

Acne is a common inflammatory disease in skin areas where sebaceous glands are largest, most numerous, and most active. In its milder types it is a more or less superficial disorder which is evidenced by slight, spotty irritations and ordinary skin hygiene is a satisfactory treatment. However, in the more inflammatory types of acne, bacterial invasion of or about the pilosebaceous follicles occurs and pustules, infected cysts and, in extreme cases, canalizing inflamed and infected sacs appear. These lesions may become extensive and leave permanent, disfiguring scars.

Acne is very common by puberty and at least 80% of teenagers are afflicted. The facial eruptions are known to cause such psychic trauma in many adolescents that they find it difficult to make personal adjustments and consequently, withdraw and self-pity occur. The sufferer may be constantly aware of the obvious facial blemishes. For these reasons a medicinal preparation and treatment are of definite benefit and may eliminate the need for psychotherapy.

REPORTED DEVELOPMENTS

To reduce the severity of acne, various forms of medication have previously been topically applied to the skin. Antibacterial soaps have been used as well as bactericidal agents such as sulfur and resorcinol. Other topical compositions have separately contained benzoyl peroxide, hexachlorophene, erythromycin or neomycin sulfate. None of these prior preparations has been completely effective.

U.S. Pat. No. 3,535,422 discloses a therapeutic composition for the treatment of acne comprising a uniform dispersion of benzoyl peroxide in a fluid medium containing water and at least one organic emollient.

U.S. Pat. No. 4,056,611 discloses a therapeutic composition for the treatment of acne comprising a stable dispersion of finely divided particles of benzoyl peroxide in an aqueous alcohol vehicle having a single phase. The single phase of the composition is non-lipid and contains a non-ionic surface active agent that is soluble in the aqueous alcohol vehicle.

U.S. application Ser. No. 60,392 filed July 25, 1979 of the present applicants, which is incorporated herein by reference, discloses use of dioctyl sodium sulfosuccinate as a stabilizing agent for benzoyl peroxide formulations and the increased stability of benzoyl peroxide in micronized form.

Prior art peroxide compositions which contain merely finely divided peroxide particles in an emulsion of water and certain select emollients provides the disadvantage that when the water content of the emulsion evaporates there remains most of the organic emollients and the large benzoyl peroxide particles on the surface of the skin near and in contact with the acne sites which may cause irritation.

Additionally, the use of large amounts of non-ionic surface active agents in such compositions unless extremely fine particles of peroxide are utilized, would cause a likelihood of irritation from the peroxide.

Also, because of the powerful oxidizing properties of the peroxide component, the inclusion of this substance is a conventional ointment or emulsion or with other active ingredients results in unstable compositions that soon display an unacceptable loss in keratolytic potency.

In accordance with the present invention, it has been discovered that a mixture on the skin of a peroxide, especially benzoyl, and erythromycin is particularly beneficial as they exert a statistically significant synergistic effect. Benzoyl peroxide inhibits the formation of free fatty acids in the skin, primarily through inactivation of extracellular lipase (via oxidation) necessary to cleave triglycerides into free fatty acids and glycerol. Erythromycin effectively reduces the concentration of *Corynebacterium acnes* (i.e., *P. acnes*), a normal anaerobic bacteria which is the prime source of the lipase. Instead of the benzoyl peroxide, which is preferred, other peroxides of organic acids may be used such as lauroyl peroxide. Instead of erythromycin, which is preferred, erythromycin derivatives may be substituted such as erythromycin stearate or glucoheptonate.

These two ingredients may be applied to the skin as a mixture or they may separately be applied to the skin. In the latter practice the erythromycin would preferably first be applied to the skin and immediately or shortly thereafter the peroxide would be applied. Or, the order of application would be reversed. If a mixture is to first be made up and then applied to the skin it is best that the mixture be made at the time of application or that the mixture be used within twenty-four hours.

The prompt use of a premix is due to the relative incompatibility of the two active agents and because of this it is advisable that the two agents be put in separate vials, bottles or other containers. However, as a feature of the present invention there is provided a novel vehicle for the active ingredients whereby the mixture of the ingredients has a surprising stability and shelf life at temperatures conventionally employed for the storage of erythromycin solutions; additionally, the novel vehicle provides a more uniform dispersion of active ingredients.

The therapeutic gel composition of the present invention must contain sufficient peroxide to be therapeutically effective, and should not contain more peroxide than can be uniformly dispersed in the vehicle to form a smoothly spreadable composition. Such considerations dictate that the composition contain at least 1% and not more than 30% by weight of peroxide, and preferably that the composition contain from about 2.5% to 15%, by weight peroxide. The peroxide constituent of the composition should be of the high purity and in the form of finely divided crystalline particles, preferably, micronized particles having a mean average particle size of less than 35 microns. Utilizing a peroxide which has been micronized provides greater stability and shelf life to the composition when used in combination with dioctyl sodium suflosuccinate as the surfactant. The gel composition of the present invention may advantageously include a further wetting agent such as the esters of polyols and sugars, the products of the condensation of ethylene oxide with fatty acids, fatty alcohols, long-chain alky phenols, long-chain mercaptans, long-chain amides, polyethers of polyhydroxylated fatty alcohols and alky polyglycol ethers in an amount of from about 3% to about 6%, by weight.

It has been surprisingly found that in an aqueous alcoholic gel vehicle the utilization of a peroxide and an erythromycin compound in combination with dioctyl sodium sulfosuccinate as the surface active agent results in a composition which displays full stability with respect to the peroxide component even when subjected to temperatures higher than those normally expected in the oridinary use of the product. Also, the mixture of the present invention upon evaporation allows a uniform release of the peroxide so as to obviate the burning and erythema experienced with other harsh formulations.

The aqueous gel composition of the present invention contains from about 1% to about 30%, and preferably from about 5% to 15%, by weight, of peroxide, especially, micronized benzoyl peroxide having a particle size of less than about 150 microns with the mean average particle size being less than about 35 microns. Dioctyl sodium sulfosuccinate which serves as a surface active agent as well as providing for the increased stability of the composition is present in the amount of about 0.1% to 2%, by weight of composition. The composition may also advantageously contain a further wetting agent in an amount of about 1.0% to about 6.0% by weight and preferably about 3% to 6% by weight.

Further advantage and objects of the present invention will become more apparent when viewed with the drawings in which:

FIG. 1 is a perspective view of a package containing two containers, one for each active agent;

FIG. 2 is a section on the line 2—2 of FIG. 1;

FIG. 3 is a section on the line 3—3 of FIG. 2, and;

FIG. 4 is a perspective view of a package containing a single jar.

A mixture of the two active ingredients may be lightly dusted on the affected skin area much in the same manner that ordinary face powder would be applied. This could be an application of either the premix shown in FIG. 4, or of the successively applied separate agents in the two containers of FIG. 1, or of a premix of the two agents of FIG. 1 made at the time of application. However, it is possible to dilute the mixture with a carrier which may be a powder, a semi-solid vehicle of creamlike consistency or a liquid such as a water emulsion or with an organic solvent, especially an aqueous mixture containing as a surfactant dioctyl sodium sulfosuccinate.

On a weight basis, the selected erythromycin and the selected peroxide should be measured out so that as applied to the skin the latter is from about one to about thirty times the weight of the former, preferably from about one to about five times. In a premix composition including a diluent to be applied to the skin, the selected erythromycin should be present at a level ranging from 0.5% to 5.0% w/w and the selected peroxide should be present at a level ranging from 1.0% to 30% w/w. A preferred concentration is about 2% to about 3% of the selected erythromycin and about 5% to about 10% of the selected peroxide.

As erythromycin is limited in its solubility, the preferred dermatologic solvents are alcohol or acetone but the composition is not limited to these liquids. In solution, erythromycin rapidly degrades, even at normal room temperature. Refrigeration somewhat extends the shelf-life of such solutions.

A preferred diluent or carrier is a hydroalcoholic gel system, but liquid suspensions and emulsions, as well as creams, ointments and powders are acceptable. Conventional pharmaceutical processes may be used in making up these common forms of medicinal, topical compositions. For instance, a premix may be placed in a capped conventional ointment or like container 9 as shown in FIG. 4, as this would minimize the stability problem. The patient should be instructed to refrigerate the preparation. Ordinarily, the jar 9 would be in a cardboard or like package 10.

For commercial preparation it is best to make up a cardboard package 5 with a cover 6, which includes two capped containers as is shown in the accompanying drawing. One container would have only the erythromycin in it and it would be large enough to accommodate all the other ingredients to later be mixed with. The other container would contain an aqueous gel benzoyl peroxide composition, with or without the solvent for the erythromycin, as well as the other ingredients to make up the topical composition. However, it has been surprisingly found that the use of dioctyl sodium sulfosuccinate as a surfactant provides stability to the composition.

The gelling agent used in this invention may be selected both as to type and quantity to give products of various viscosities. In the preferred form of this invention, the gelling agent is selected so as to produce an elegantly formed and stable gel. A variety of gelling agents may be used for the present purposes. However, preferred gelling agents are pure micro-crystalline cellulose, colloidal magnesium aluminum silicate, hydroxypropyl methyl cellulose and the so-called hydroxylated vinylic polymers, particularly, those disclosed in U.S. Pat. No. 2,798,053. Among those hydroxylated vinylic polymers of special interest herein are described generally as interpolymers of a monomeric monoolefinic acrylic acid, and from about 0.1% to about 10% by weight based on the total monomer of a monomeric polyether of an oligosaccharide in which the hydroxyl groups which are modified are esterified with allyl groups with said polyether containing at least two allyl ether groups per oligosaccharide molecule. Commercially available interpolymers of this type are marketed under the trade name Carbopols ®. These are described as being polymers of acrylic acid cross-lined with about 1% of a polyallyl ether of sucrose having an average of about 5.8 allyl groups for each sucrose molecule. These polymers have molecular weight in the order of magnitude of 1,000,000. Such polymers are available from the B. F. Goodrich Chemical Company and are sold under such trademarks as Carbopol ® 934, Carbopol ® 940, and Carbopol ® 941.

The quantity of gelling agent that may be contained in the present compositions may also vary somewhat. Ordinarily, this will constitute about 0.1% to about 15% by weight, and preferably about 0.5% to about 3% by weight, based on the total weight of the finished composition.

As mentioned above, the simplest topical preparation is a mixture of powdered benzoyl peroxide and erythromycin with no diluent, but it would have to be sparingly applied to the skin. Instead of applying a premixutre of them, one may first be applied to the skin and then the other would be applied with slight rubbing to mix them on the skin. A suitable, simplified preparation is the following:

EXAMPLE 1

| Benzoyl peroxide | 1–35 w/w |
|---|---|
| Calcium phosphate | 63–98.5 w/w |
| Erythromycin | .5–5 w/w |

These ingredients are intimately mixed together and dusted on the affected skin area, from one to four times daily. It could be sold in the container 9 of FIG. 4.

If a liquid preparation is desired, the following is a simplified composition which may be made and applied to the skin from one to four times daily as though it were an ordinary face lotion. It could be sold in one of the bottles of FIG. 1 with or without the carton 5.

EXAMPLE 2

| Ethanol | Q.S.–100 w/w |
|---|---|
| Erythromycin | 0.5–5 w/w |
| Benzoyl peroxide | 1–30 w/w |

Other examples which are representative of the invention are the following:

EXAMPLE 3

Lotion

In a first container 7 are placed the following ingredients, by weight:

| | 100% |
|---|---|
| Ethoxylated cetyl-stearyl alcohol | 7.00% |
| Cetyl alcohol | 0.75% |
| Isopropyl myristate | 5.00% |
| Butylated hydroxyanisole | 0.10% |
| Polyoxyl 40 stearate | 0.25% |
| Water, deionized or distilled | 68.80% |
| Propylene glycol | 3.00% |
| Benzoyl peroxide | 5.00% |
| Acetone | 10.00% |
| Dioctyl sodium sulfosuccinate | 0.10% |

In a second container 8 is placed the following ingredient by itself, the container being large enough to accommodate a quantity of a solvent, preferably, ethanol or acetone, in the ration of 3 cc./20 grams of the composition in container 7.

| Erythromycin | 2% w/w of the contents of container 7 |
|---|---|

Both containers are put in a single marketable package such as 5 with the instructions that the contents of container 8 is added to container 7 and be thoroughly mixed. Alternately, to container 8 having the erythromycin is added 3 cc. ethanol per each 20 grams of material in container 7. The solution of erythromycin in ethanol is then added to container 7 and thoroughly mixed. This would either be done by the pharmacist or by the patient. The patient would apply the lotion to the skin as though it were an ordinary lotion from one to four times daily.

A variation of Example 3 is to further dilute container 8 with the same solvent so that some of the contents of container 7 would first be applied to the skin and then some of the contents of container 8 would be applied to the skin so that the mixture occurs on the skin. This eliminates loss due to the shelf life or storage of the mixture.

EXAMPLE 4

Cream

In a first container 7 are placed the following ingredients, by weight:

| Ethoxylated cetyl-stearyl alcohol | 15.00% |
|---|---|
| Cetyl alcohol | 1.25% |
| Isopropyl myristate | 5.00% |
| Butylated hydroxyanisole | 0.10% |
| Polyoxyl 40 stearate | 0.25% |
| Water, deionized or distilled | 60.60% |
| Propylene glycol | 3.00% |
| Benzoyl peroxide | 5.00% |
| Acetone | 10.00% |
| Dioctyl sodium sulfosuccinate | 0.10% |

In a second container 8 is placed the following ingredient by itself, the container being large enough to accommodate a quantity of a solvent, preferably, ethanol or acetone, in the ration of 3 cc./20 grams of the composition in container 7.

| Erythromycin | 3% w/w of the contents of container 7. |
|---|---|

The explanation for sale and use in Example 3 applies to this cream. As the preparation is of creme consistency the containers 7 and 8 should have wide mouths to facilitate mixing and removal of the creme.

EXAMPLE 5

Gel

Container 7 has in it the following, by weight:

| Water, deionized or distilled | 54.65% |
|---|---|
| Colloidal Bentonite | 2.50% |
| Carboxy vinyl polymer (acid form) | 1.00% |
| Dioctyl sodium sulfosuccinate | 1.00% |
| Diisopropanolamine | 0.75% |
| Ethyl alcohol, 200° | 35.00% |
| Butylated hydroxyanisole | 0.10% |
| Benzoyl peroxide (micronized) | 5.00% |

Container 8 has in it only the following:

| Erythromycin | 3% w/w of the contents of container 7. |
|---|---|

The explanation for packaging in wide mouth containers, and compounding at the time of dispensing in Example 4 applied to this gel.

EXAMPLE 6

Suspension

Container 7 has in it the following, by weight:

| | |
|---|---|
| Water, deionized or distilled | 56.97% |
| Colloidal Bentonite | 1.50% |
| Carboxyl vinyl polymer (acid form) | 0.25% |
| Dioctyl sodium sulfosuccinate | 1.00% |
| Diisopropanolamine | 0.18% |
| Ethyl alcohol, 200° | 35.00% |
| Butylated hydroxyanisole | 0.10% |
| Benzoyl peroxide (micronized) | 5.00% |

Container 8 has in it only the following:

| | |
|---|---|
| Erythromycin | 2% w/w of the contents of container 7. |

The explanation for use in Example 3 applies to this suspension.

EXAMPLE 7

In any of the Examples 3 to 6, the amount of benzoyl peroxide is reduced or increased within the range of 1% to 30% w/w of the container 7 contents, the amount of water being proportionately increased or reduced. The amount of erythromycin in container 2 should be measured to amount of one-fifth to two times w/w of the measured benzoyl peroxide.

EXAMPLE 8

In any of the above examples another organic acid peroxide is substituted for the benzoyl peroxide.

EXAMPLE 9

In any examples 3 to 6, water is substituted for acetone and or lower alkanol such as methanol, ethanol, etc.

EXAMPLE 10

In any of the above examples an erythromycin derivative is substituted for the erythromycin.

These examples are shown as illustrations of this invention and are not to be construed as limitations thereof. Thus, for example, certain of the above ingredients may be substituted for other ingredients which would be well known to the skilled artisan in dermatological preparations. Varying amounts of other ingredients or alternate excipients may be added or interchanged as the artisan sees pits and falls within the meaning for this invention. The use of acetone or alcohol may also be changed depending on the wishes of the artisan.

EXAMPLE 11

(A) 495.0 mg of purified water was mixed and 15.0 mg or Carbopol ® 940 (a carboxyl vinyl polymer, acid form, of B. F. Goodrich Co.) were added to the water while stirring. Stirring of the mixture was contained for 45 minutes. Then 4.095 mg of sodium hydroxide in 4.91 ml of purified water was added thereto. Stirring of the mixture was continued for 10 minutes, wherupon 150.0 mg of ethyl alcohol, 0.50 mg of perfume and 0.50 mg of methyl salicylate was added. The the stirred mixture was then added a mixture comprising 210.0 mg of wet pack micronized benzoyl peroxide (50% benzoyl peroxide-50% water), 2.0 mg of dioctyl sodium sulfosuccinate, 41.0 mg of alkyl polyglycol ether and 41.0 mg of purified water. The mixture was stirred for 30 more minutes Until a smooth and elegant gel mixture was obtained.

(B) Three samples of gel formulation from Part A weighing approximately 20.0 gm of gel were mixed with 0.8 gm Erythromycin in 3.0 ml abs. EtOH to yield a total weight of 23.25 gm. Each gram of sample contained 34.40 mg of Erythromycin.

On the initial day of the experiment [0 time] three 20.0 gm gel samples of active gel were mixed with the Erythromycin-EtOH soln. for three minutes with a plastic spatula and allowed to rest for approximately 15 minutes.

A 1.0 gm sample in duplicate was removed from each of the three samples and placed with first addition MeOH and second 0.1M pH 8.0 $PO_4$ buffer for a total of 200 ml volume. This mixture was blended on a blender at low speed for three minutes at room temperature. The solution was allowed to lose its foam layer by waiting five minutes and then a 1.0 ml sample was removed and Q.S.'d to 109 ml with 0.1M $PO_4$ pH 8.0 buffer.

This was placed in the stainless steel cylinders that had been previously dropped onto seeded Agar plates. The 4 ml top seed layer contained 1.5 ml stocks of *S. lutea* (at 25% light transmission in a 1:40 dilution of standardizing solution) per 100 ml of the Agar.

The plates also had appropriate reference standards of $\mu$g/ml Erythromycin solution in alternate cylinders.

The standard curve plates as well as test plates were incubated at 35° C. for 18 hours. The cylinders were removed and zone sizes read and compared with standard zone sizes.

EXAMPLE 12

(A) 536.0 mg of purified water was mixed and 15.0 mg or Carbopol ® 940 (a carboxyl vinyl polymer, acid form, of B. F. Goodrich Co.) were added to the water while stirring. Stirring of the mixture was contained for 45 minutes. Then 4.095 mg of sodium hydroxide in 4.91 ml of purified water was added thereto. Stirring of the mixture was continued for 10 minutes, whereupon 150.0 mg of ethyl alcohol, 0.50 mg of perfume and 0.50 mg of methyl salicylate was added. To the stirred mixture was then added a mixture comprising 210.0 mg of wet pack micronized benzoyl peroxide (50% benzoyl peroxide-50% water), 2.0 mg of dioctyl sodium sulfosuccinate and 41.0 mg of purified water. The mixture was stirred for 30 more minutes until a smooth and elegant gel mixture was obtained.

(B) Samples of gel formulation from Part A weighing approximately 20.0 gm of gel were mixed with 0.5 gm Erythromycin in 3.0 ml ethanol to yield a total weight of 22.87 gm and placed in containers. Each gram of sample contained about 21.85 mg of Erythromycin. The resultant product was suitable for use in the treatment of acne.

EXAMPLE 13

Following the procedure of Example 12, the following gel formulation was prepared:

| | |
|---|---|
| Benzoyl peroxide (micronized) | 5.46% by weight |
| Erythromycin | 2.00% by weight |
| Ethyl alcohol | 44.10% by weight |
| Polyoxyethylene lauryl ether | 6.00% by weight |
| Colloidal magnesium aluminum silicate | 2.50% by weight |
| Hydroxypropylmethylcellulose | 1.00% by weight |
| Citric acid | 0.05% by weight |
| Dioctyl sodium sulfosuccinate | 0.02% by weight |
| Water | Q.S. |

The resultant product had good stability and was effective for use in the treatment of acne.

What is claimed is:

1. A therapeutic aqueous gel composition comprising:
   about 2.5 to about 15% by weight of micronized benzoyl peroxide having particle size of less than about 150 microns; and
   about 0.5 to about 5% of an erythromycin compound selected from the group consisting of erythromycin and its stearate, and glucoheptonate derivatives; and
   wherein the amount of said peroxide is about one-half to about thirty times the weight of said erythromycin compound.

2. A composition according to claim 1 wherein said erythromycin compound is erythromycin.

3. A composition according to claim 2 wherein said erythromycin is present in said composition in an amount of about 2 to about 3% by weight.

4. A composition according to claim 3 including a gelling agent selected from the group consisting of colloidal magnesium aluminum silicate, hydroxypropylmethylcellulose, microcrystalline cellulose, and hydroxylated vinyl polymers.

5. A therapeutic aqueous alcoholic gel composition suitable for the treatment of acne comprising:
   about 5 to about 10% by weight of micronized benzoyl peroxide having a particle size of less than about 150 microns and having a mean average particle size of less than about 35 microns;
   about 2 to about 3% by weight of erythromycin; and
   about 0.1% to about 15% by weight of a hydroxylated vinyl polymer gelling agent.

6. A composition according to claim 5 wherein the amount of said gelling agent is about 0.5% to about 3% by weight.

7. A method for the treatment of acne in humans afflicted therewith comprising the topical administration of a composition according to claim 1.

* * * * *